United States Patent
Flohr et al.

(10) Patent No.: US 9,273,419 B2
(45) Date of Patent: Mar. 1, 2016

(54) FLUID ACQUISITION LAYER

(75) Inventors: Andreas Flohr, Kronberg (DE); Paschalia Makavou-Jennen, Hofheim am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 2076 days.

(21) Appl. No.: 11/600,691

(22) Filed: Nov. 16, 2006

(65) Prior Publication Data
US 2007/0118087 A1    May 24, 2007

(30) Foreign Application Priority Data
Nov. 21, 2005    (EP) .................................. 05111029

(51) Int. Cl.
| | |
|---|---|
| *D04H 13/00* | (2006.01) |
| *A61F 13/537* | (2006.01) |
| *A61L 15/22* | (2006.01) |
| *D04H 1/425* | (2012.01) |
| *D04H 1/435* | (2012.01) |
| *D04H 1/50* | (2012.01) |
| *D04H 1/587* | (2012.01) |
| *D04H 1/593* | (2012.01) |
| *D04H 1/732* | (2012.01) |

(Continued)

(52) U.S. Cl.
CPC ............ *D04H 13/00* (2013.01); *A61F 13/5376* (2013.01); *A61L 15/225* (2013.01); *D04H 1/425* (2013.01); *D04H 1/435* (2013.01); *D04H 1/50* (2013.01); *D04H 1/587* (2013.01); *D04H 1/593* (2013.01); *D04H 1/732* (2013.01)

(58) Field of Classification Search
CPC .......... D04H 13/00; D04H 1/43; A61F 13/55; A61F 13/56
USPC .......................................................... 604/358
See application file for complete search history.

(56) References Cited

U.S. PATENT DOCUMENTS

| | | | | |
|---|---|---|---|---|
| 3,860,003 | A | * | 1/1975 | Buell ...................... 604/385.25 |
| 4,226,237 | A | | 10/1980 | Levesque |
| 4,834,735 | A | | 5/1989 | Alemany et al. |

(Continued)

FOREIGN PATENT DOCUMENTS

| | | |
|---|---|---|
| GB | 2121069 A | 12/1983 |
| WO | WO-95/13776 A1 | 5/1995 |

(Continued)

OTHER PUBLICATIONS

American Chemical Society, Contact Angle, Wettability, and Adhesion, ©1964.

(Continued)

*Primary Examiner* — Tatyana Zalukaeva
*Assistant Examiner* — Ilya Treyger
(74) *Attorney, Agent, or Firm* — Andrew J. Mueller (57) ABSTRACT

A liquid acquisition material for use in an absorbent article. The liquid acquisition material having first fibers and second fibers. The first fibers are chemically cross-linked cellulose fibers and the second fibers are selected from the group consisting of: polyethylene, polypropylene, polyester, rayon, lyocell, and mixtures thereof. The liquid acquisition material has a total dry weight, the first fibers have a first dry weight, and the second fibers have a second dry weight. The first dry weight is from 30 to 95 percent of the total dry weight and the second dry weight is from 5 to 70 percent of the total dry weight.

9 Claims, 5 Drawing Sheets

(51) Int. Cl.
*D04H 1/43* (2012.01)
*A61F 13/56* (2006.01)

(56) References Cited

U.S. PATENT DOCUMENTS

| | | | |
|---|---|---|---|
| 4,950,264 A | | 8/1990 | Osborn, III |
| 5,037,416 A | | 8/1991 | Allen et al. |
| 5,134,007 A | * | 7/1992 | Reising et al. ............... 428/78 |
| 5,137,537 A | * | 8/1992 | Herron et al. ............... 8/120 |
| 5,151,092 A | | 9/1992 | Buell et al. |
| 5,269,775 A | | 12/1993 | Freeland et al. |
| 5,348,547 A | * | 9/1994 | Payne et al. ............... 604/378 |
| 5,569,234 A | | 10/1996 | Buell et al. |
| 5,625,222 A | | 4/1997 | Yoneda et al. |
| 5,840,787 A | * | 11/1998 | West et al. ............... 524/35 |
| 5,873,867 A | | 2/1999 | Coles et al. |
| 5,990,377 A | * | 11/1999 | Chen et al. ............... 604/381 |
| 6,004,306 A | | 12/1999 | Robles et al. |
| 6,207,278 B1 | | 3/2001 | Jewell et al. |
| 6,458,460 B1 | | 10/2002 | Griffiths et al. |
| 6,821,940 B2 | * | 11/2004 | Bullock et al. ............... 510/439 |
| 7,138,561 B2 | | 11/2006 | Fuchs et al. |
| 7,750,203 B2 | * | 7/2010 | Becker et al. ............... 604/366 |
| 2003/0097104 A1 | | 5/2003 | Gilbert |
| 2003/0105190 A1 | | 6/2003 | Diehl et al. |
| 2003/0135182 A1 | * | 7/2003 | Woon et al. ............... 604/378 |
| 2006/0222675 A1 | * | 10/2006 | Sabnis et al. ............... 424/405 |

FOREIGN PATENT DOCUMENTS

| | | |
|---|---|---|
| WO | WO-97/00354 A1 | 1/1997 |
| WO | WO-98/22279 A1 | 5/1998 |
| WO | WO-99/63922 A1 | 12/1999 |

OTHER PUBLICATIONS

Textile Research Journal, 37 (1967) pp. 356-366.
Textile Science and Technology, vol. 7, Chapter II, pp. 29-84.
International Search Report, dated May 8, 2007, 6 pages.

\* cited by examiner

FLUID ACQUISITION LAYER

FIELD OF THE INVENTION

The present invention relates to absorbent articles such as disposable diapers, sanitary napkins and panty liners. More specifically, the present invention relates to acquisition layers and materials for such acquisition layers, which are very suitable to be used with thin products comprising a relatively high concentration of super-absorbent polymer material.

BACKGROUND OF THE INVENTION

Disposable absorbent articles are broadly available and consumers generally prefer high performance for the collection and retention of menses (in the case of sanitary napkins or panty liners) or for the collection and retention of urine and fecal material (in the case of e.g. disposable diapers). However, consumers that expect a superior absorbency behaviour may also place more emphasis on the wearing comfort of such articles, and namely on the dryness of those articles.

Typically, such articles comprise multiple absorbent members, at least one member being primarily designed to store liquid, and at least one other member primarily designed to acquire and/or distribute liquid.

At least the storage member will often comprise super-absorbent material, which may be admixed with the traditionally used pulp fiber material. Such super-absorbent materials can absorb many times (e.g. 10, 20, or 30 times) their own weight and are therefore very helpful when designing an article of improved fluid handling properties. Many recent products employ higher and higher concentrations of super-absorbent materials, that is concentrations in excess of 50% of the total weight of the storage member. These products achieve a high absorbing capacity with a very thin storage member and are thereby typically overall thin products. While super-absorbent materials can store very large amounts of liquid, they are often not able to distribute the liquid from the point of impact to more remote areas of the absorbent article and to acquire the liquid as fast as it may be received by the article.

For this reason acquisition members are used, which provide for the interim acquisition of large amounts of liquid and which often also allow for the distribution of liquid. Thereby the acquisition member plays an important role in using the whole absorbent capacity provided by the storage member.

Materials suitable to meet the above outlined requirements for a liquid acquisition layer must meet these requirements not only in standard or ideal conditions, but in a variety of conditions, namely at different temperatures and pressures, occurring in use, but also during storage and handling.

WO 98/22279 (Flohr et al.) discloses acquisition layers for improved liquid handling in absorbent articles. As one fluid handling material fibrous materials, which can be carded, are disclosed. These fibers are chemically bonded by a resin. According to this disclosure a resin bonded acquisition layer can be combined with a layer of crosslinked cellulose material.

WO 97/00354 (Cook et al.) discloses a process for obtaining such cellulose material, according to which brighter individualized fibers of reduced odour can be obtained, which are cross-linked with a polycarboxylic acid.

U.S. Pat. No. 5,137,537 (Herron et al.) discloses the use of conventional pulp fibers in combination with cross-linked pulp fibers for use in an absorbent article.

For the use in specific absorbent articles, such as tampons US 2003/0097104 A1 (Gilbert) discloses the use of a wicking overwrap, which allows good acquisition and wearing comfort. This wicking overwrap can comprise synthetic fibers and rayon fibers in a ratio from about 90:10 to about 30:70.

The present invention provides an absorbent article, which has improved liquid handling characteristics as compared to the above disclosed articles.

In a further aspect present invention provides an article, which is more comfortable to wear, and which in particular provides superior dryness.

In a yet further aspect, the present invention provides fluid acquisition layers for improved liquid handling characteristics, namely for use with storage layer comprising a high concentration of super absorbent polymers and with a further (typically topmost) liquid layer comprising resin bonded fibers.

SUMMARY OF THE INVENTION

A liquid acquisition material for use in an absorbent article, said material comprising at least first fibers and second fibers, wherein said first fibers are chemically cross-linked cellulose fibers and said second fibers are selected from the group consisting of: polyethylene, polypropylene, polyester, rayon, lyocell, and mixtures thereof, wherein said liquid acquisition material has a total dry weight and the first fibers have a first dry weight, and the second fibers have a second dry weight, wherein the first dry weight is from 30 to 95 percent of said total dry weight and the second dry weight is from 5 to 70 percent of the total dry weight.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like.

"Disposable" is used herein to describe articles that are generally not intended to be laundered or otherwise restored or reused i.e., they are intended to be discarded after a single use and, possibly, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

The terms "thickness" and "caliper" are used herein interchangeably.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven", "nonwoven fabric" and "nonwoven web" are used interchangeable.

Absorbent Articles

Figure 1:
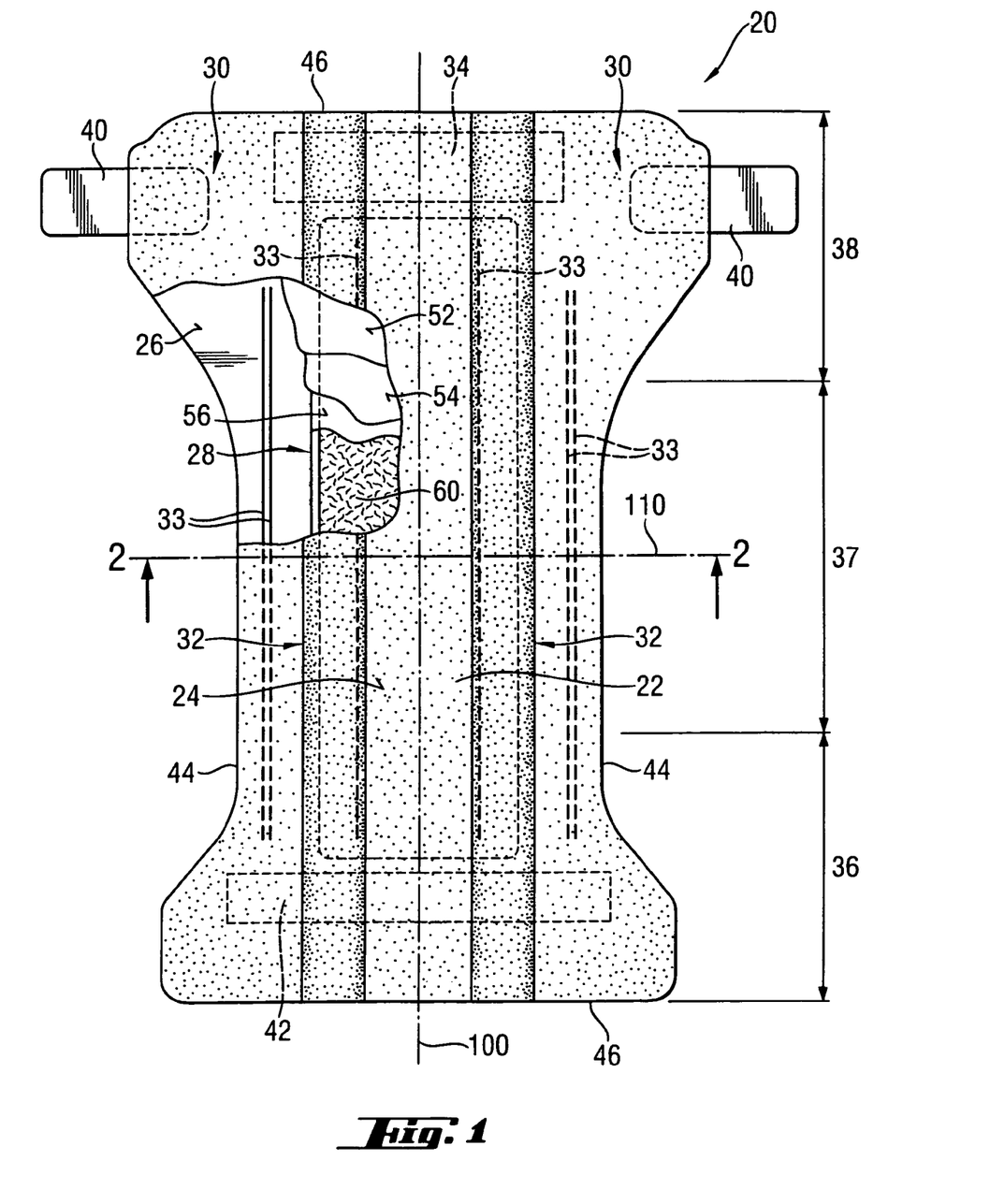
FIG. 1 is a top plan view of a disposable diaper, with the upper layers partially cut away.

FIG. 1 is a plan view of a diaper 20 as an embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis can further include side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 attached to the rear waist region 38 and comprising a landing zone 42 attached to the front waist region 36. The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. The topsheet 24, the backsheet 26, and the absorbent core 28 may be assembled in a variety of well-known configurations. Specific diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. Often, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 attached to the rear waist region 38. In one embodiment the fastening system further comprises a landing zone 42 attached to the front waist region 36. The fastening member is attached to the front waist region 36, often to the landing zone 42, to form leg openings and an article waist.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. In some embodiments, the materials making up the fastening device are flexible. The flexibility is designed to allow the fastening system to conform to the shape of the body and thus, reduces the likelihood that the fastening system will irritate or injure the wearer's skin.

Figure 2:
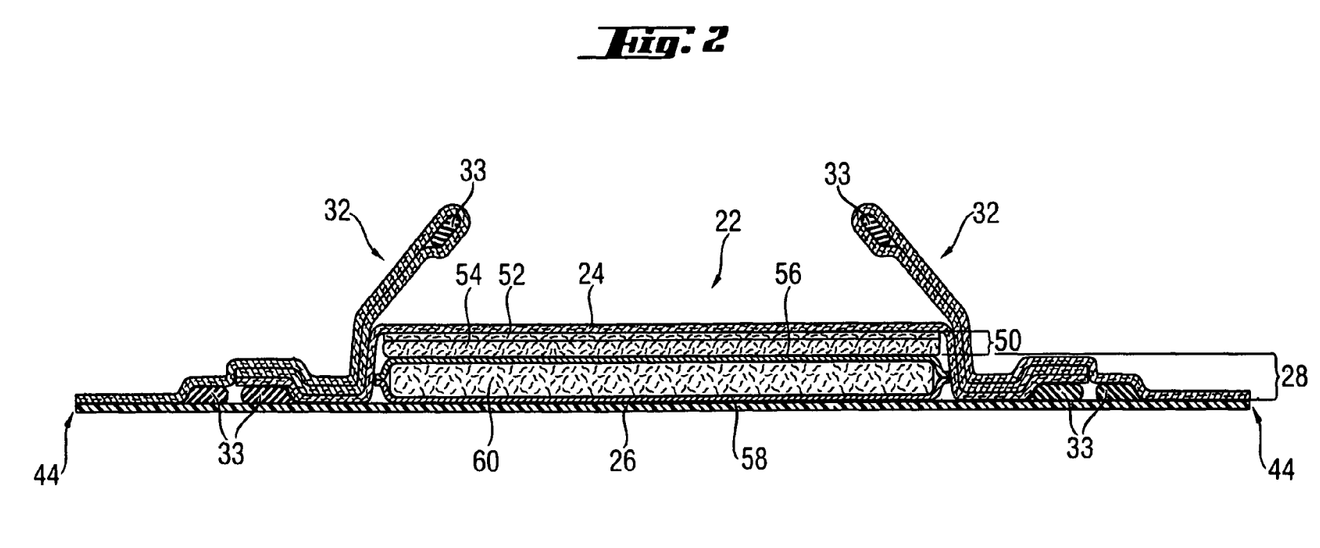
FIG. 2 is a cross-sectional view of the disposable diaper shown in FIG. 1.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core may comprise an acquisition system 50, which comprises an upper acquisition layer 52 facing towards the wearer and a lower acquisition layer 54. In one embodiment the upper acquisition layer comprises a nonwoven fabric whereas the lower acquisition layer comprises a mixture of chemically stiffened, twisted and curled fibers, high surface area fibers and thermoplastic binding fibers. In another embodiment both acquisition layers are provided from a non-woven material, which can also be hydrophilic. The acquisition layer can be in direct contact with the storage layer 60.

Acquisition members according to the present invention may comprise the acquisition system 50 of a diaper as described. In one embodiment, the acquisition members are comprised by the upper acquisition layer 52. In one embodiment of the present invention the upper acquisition layer 52 consists of the claimed acquisition member.

The storage layer 60 can be wrapped by a core wrap material. In one embodiment the core wrap material comprises a top layer 56 and a bottom layer 58. The top layer 56 and the bottom layer 58 can be provided from a non-woven material. One useful material is a so-called SMS material, comprising a spunbonded, a melt-blown and a further spunbonded layers. The top layer 56 and the bottom layer 58 may be provided from two or more separate sheets of materials or they may be alternatively provided from a unitary sheet of material. Such a unitary sheet of material may be wrapped around the storage layer 60, e.g. in a C-fold. The top layer 56 and the bottom layer 58 may also be joined to each other, for example along their periphery. In another option both layers are joined along their longitudinal peripheries, in other embodiments they are joined along the transversal peripheries, or along the longitudinal and the transversal peripheries. The joining can be achieved my multiple means well known in the art, e.g. by adhesive means, using a continuous or a discontinuous pattern, for example a linear or curvilinear pattern.

The storage layer 60 typically comprises fibrous materials, mixed with superabsorbent, absorbent gelling materials. Other materials described above as suitable for the absorbent core 28 may also be comprised.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibers may be of natural or man-made origin. They may be staple or continuous filaments or be formed in situ.

Nonwoven fabrics can be formed by many processes such as meltblowing, spunbonding, carded. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Man-made fibers can either be synthetic fibers or they can be derived from natural fibers. Man-md. or not. Examples of man-made fibers, which are not synthetic but which are derived from natural fibers, include but are not limited to rayon and lyocell (tradename "Tencel"®), both of which are derived from cellulose, a natural polysaccharide fiber. Synthetic fibers, which are not derived from natural fibers, can be derived from other natural sources or from mineral sources. Example synthetic fibers not derived from natural sources include but are not limited to polysaccharides such as starch. Example synthetic fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers, which can be laid into webs at a distinctly subsequent point in time. Example direct extrusion processes include but are not limited to: spunbonding, meltblowing, solvent spinning, electro-spinning, and combinations thereof typically forming layers.

Example "laying" processes include wet-laying and air-laying (the latter occasionally also referred to as dry-laying). Example air-laying processes include but are not limited to airlaying, carding, and combinations thereof typically forming layers. Combinations of the above processes yield non-wovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermobonding by use of heated calendar rolls.

All of the above described fibers and manufacturing techniques can be useful for providing an acquisition member according to the present invention.

Useful Acquisition Members for the Upper Acquisition Layer

For use as an upper acquisition layer 52 any material comprising a multitude of fibers and a binder, namely any nonwoven material as described above is suitable for providing a liquid acquisition layer according to the present invention. The respective material must provide good recovery regarding the application and removal of external pressure.

While a large variety of fibers and binders are suitable, it has been found that certain materials provide a better recovery than other materials and are therefore useful as materials according to the present invention.

Useful fibers according to the present invention are polyester fibers, such as PET fibers. The acquisition materials have been found to work best if a blend of different fibers is used. While a blend of 3, 4, 5 or more different fibers can be used, often a blend of two fibers can be used. Such blend may comprise at least 10, 20, 30, 40, 50, 60, 70, 80, or 90 weight % of a first type and the remaining weight % portion of a second type of fiber. Useful for the present invention is a 50:50 blend of fibers, i.e. 50 weight percent of a first type of fibers is blended with 50 weight percent of a second type of fibers. In some embodiments, at least the second type of fibers will exhibit a spiral-crimp. As used herein, a spiral-crimp is any three-dimensional crimp and often one wherein the fibers substantially assume a helical shape. The first type of fibers will often have a higher crimp value as the second type of fibers. Useful crimp values for the third type of fibers are 8-12 crimps per inch (cpi), for example 9-10 cpi. For the second type of fibers 4-8 cpi are useful, for example 5-7 cpi. One useful type of fibers useful in the present invention are so-called bi-component fibers, where individual fibers are provided from different materials, usually a first and a second polymeric material. Often, at least one type of fibers or two or more types of fibers are crimped. For the first type of fibers a 2D crimp or "flat crimp" is useful. For the second type of fibers a 3D or spiral-crimp is useful. It is believed that the use of side-by-side bi-component fibers is beneficial for imparting a spiral-crimp to the fibers.

While any of the above-described manufacturing processes for non-wovens are suitable to provide an acquisition member in accordance with the present invention, a useful manufacturing process for such an acquisition member in both carding resin-bond technology as described in WO 98/22279. As part of this process the binder will be cured and dried after having been applied to the web.

The materials of the present invention can be stabilized by a latex binder, for example a styrene-butadiene latex binder (SB latex). Processes for obtaining such lattices are known, for example, from EP 149 880 (Kwok) and US 2003/0105190 (Diehl et al.). Useful SB lattices, however, are obtained in using more than 10 weight % of a mono-, or bi-carboxylic acid, and will herein be referred to as having a carboxylation level of more than 10%. Useful SB latices will have a carboxylation level from 10% to 25%, for example 10% to 20%. Depending on the ultimate application of the binder level in excess of 12%, 14% or 16% can be useful. Suitable SB latex is available under the trade name GENFLO™ 3160 (OMNOVA Solutions Inc.; Akron, Ohio).

Useful Acquisition Members for the Lower Acquisition Layer

For the lower acquisition layer, liquid acquisition materials as described hereinafter and in the claims are useful.

Useful Liquid Acquisition Materials

Liquid acquisition materials according to the present invention comprise at least two types of fibers, first fibers and second fibers. According to the present invention first fibers are chemically cross-linked cellulose fibers. The second fibers can be selected from a number of materials, in particular man-made fibers can be used, namely from the group consisting of polyethylene, polypropylene, polyester, rayon, lyocell, and mixtures thereof. Optionally the liquid acquisition material may also comprise further fibers, for example, third fibers, fourth fibers, and so forth. Depending on the intended use of the liquid acquisition material, in particular for example its position within an absorbent article, a certain weight percentage of first fibers and second fibers is to be selected. Generally, the first fibers can be present in an amount from 30 to 95% of the total weight of the acquisition material and the second fibers can be present in an amount from 5 to 70% of the total weight. For example, the first fibers can be present in an amount from 70 to 95%, or 80 to 90%. For example, the second fibers can be present in an amount from 5 to 30%, or 10 to 20%.

A useful material for the second fibers is polyester.

While any suitable cross-linking agent can be used to chemically cross-link the first fibers, useful cross-linking agents are polycarboxylic acid, for example citric acid. Polyacrylic acids can also be used. The liquid acquisition material can be provided in the form of a non-woven, which can be best integrated into an absorbent article—for which the liquid acquisition material is often used. Among the non-woven materials, air-laid materials are often useful.

A relevant attribute of such acquisition materials is the Medium Desorption Pressure, MDP, of the material. In one aspect, it is related to the acquisition speed. The MDP is a measure of the capillary pressure that is required to dewater the acquisition structure to 50% of its capacity at 0 cm capillary suction height as derived from the Capillary Sorption test, hereinafter described. Generally, a relatively lower MDP is useful. The lower MDP allows the distribution material to more efficiently drain the acquisition material. The reduced desorption pressure also allows the distribution material to utilize more of its capillary suction to distribute liquid to the storage material. Without wishing to be bound by theory, a given distribution material will have a definable capillary suction. The ability of the distribution material to move liquid vertically via capillary forces will be directly impacted by the opposing capillary forces associated with the desorption of the acquisition material. Minimizing these capillary forces, desorption of the acquisition layer, will positively impact the performance of the distribution material. Therefore, it is the intent to have an acquisition material with an MDP corresponding to a height of less than 20.5 cm, or less than 19 cm or less than or about 18 cm. These materials provide for fast acquisition. However, the lower acquisition layer must also have adequate capillary absorption suction in order to drain the layers above (upper acquisition layer and topsheet, in particular) and to temporarily hold liquid until the liquid can be partitioned away by the other core components. Therefore, materials can have a minimum MDP which should correspond to a height of greater than 5 cm.

In a further relevant aspect, the liquid acquisition materials according to the present invention normally achieve a high fluid uptake. Fluid uptake is measured in grams of absorbed fluid per gram of absorbent material and is expressed by the value of "maximum uptake". A high fluid uptake corresponds therefore to a high capacity of the material and is beneficial, because it ensures the complete acquisition of fluids to be absorbed by an acquisition material.

EXAMPLES

To illustrate the benefits of the present invention a number of representative example liquid acquisition material has been provided and been subjected to tests. As a first example, and reference example, an air-laid material comprising chemically cross-linked cellulose fibers has been provided: Citric acid has been used as the cross-linker. As this sheet comprises 100% weight percent of chemically cross-linked cellulose fibers it is not an example of a material according to the present invention. It is referred to as Example 0.

As a further example, example 1, 70% of chemically cross-linked cellulose fibers (herein also referred to as CS10) have been mixed with 10 weight percent of polyester (PET) and with 20% of untreated pulp fibers.

Example 2 has been prepared by 70% chemically cross-linked cellulose fibers, 20% lyocell fibers and 10% PET fibers.

Example 3 has been prepared from 68% chemically cross-linked cellulose fibers, 16% untreated pulp fibers, and 16% PET fibers.

All of the examples including the reference example 0 have been prepared by the same technique. All are air-laid non-wovens.

TABLE 1

| | MDP (cm of saline) | Maximum Uptake (gram per gram) | MDP improvement vs. reference absolute/% | Maximum Uptake improvement vs. reference absolute/% |
|---|---|---|---|---|
| Example 0 (Reference) | 21.0 | 13.0 | — | — |
| Example 1 | 18.1 | 12.8 | 2.9/13.8% | 0.2/1.5% |
| Example 2 | 17.8 | 13.5 | 3.2/15.2% | 0.5/3.9% |
| Example 3 | 18 | 13.9 | 3.0/14.3% | −0.9/−6.9% |

The results for maximum uptake and MDP show that the mixture of different fibers provides an improvement over the reference example. For MDP all samples show a considerable improvement between 13% and about 15%. It should be noted that such MDP improvement has a major impact of the overall absorbent article. Only if an acquisition material allows for desorption of liquid, this liquid can be stored in the storage area, such that the there available capacity is used and thereby the overall capacity of the absorbent article is increased. A high MDP value also ensures that the liquid redistribution is achieved fast, which contributes to the overall dryness of the article after having been subjected to a high amount of liquid. This is particularly beneficial for high capacity cores, such as cores with a high AGM concentration.

In a further aspect, the fluid uptake is improved in example 1 and 3 versus the reference example. As it is apparent from example 2 it is also possible to design an acquisition material which has highly improved MDP values but slightly lesser fluid uptake values. Untreated pulp is employed in example 2 is a relatively inexpensive material, which normally has absorption characteristics much inferior to cross-linked cellulose. When combined, however, with fibers like PET, the MDP value can be still substantially increased at the expense only of a moderate decrease of the uptake value.

Capillary Sorption Test for Determine Medium Desorption Pressure and Maximum Uptake The purpose of this test to measure the capillary sorption absorbent capacity, based on the test the medium desorption pressure and the maximum uptake of the materials can be determined.

Capillary Sorption Test

Capillary sorption is a fundamental property of any absorbent that governs how liquid is absorbed into an absorbent structure as a function of hydrostatic pressure. The experiment consist of measuring the capillary pressure during a cycle of fill up (absorption) and drainage (desorption) by systematically lowering or raising the height of the sample relative to the test fluid reservoir.

The method for determining capillary sorption is well recognized. See A. A. Burgeni and C. Kapur, "Capillary Sorption Equilibria in Fiber Masses," Textile Research Journal, 37 (1967), pp. 356-366, and P. K. Chatterjee, Absorbency, Textile Science and Technology Vol. 7, Chapter II, "Mechanism of Liquid Flow and Structure Property Relationships", pp. 29-84, Elsevier Science Publishers B.V., 1985 for a discussion of the method for measuring capillary sorption of absorbent structures.

Principle

A porous glass frit is connected via an uninterrupted column of fluid to a fluid reservoir, monitored on a balance. The test fluid is 0.9% saline. The sample, mounted on the porous glass frit, is maintained under constant confining pressure during the experiment. As the porous structure absorbs/desorbs fluid upon demand, the weight in the balance fluid reservoir is recorded to determine equilibrium capacity as a function of capillary suctions (i.e., hydrostatic tensions). Absorption occurs during the incremental lowering of the frit (i.e. decreasing capillary suction). Desorption occurs during the incremental raising of the frit (i.e., increasing capillary suction). These values are then corrected for the capillary sorption of the actual porous frit and any evaporation of fluid during the experiment.

Description of Capillary Sorption System

Figure 3A:
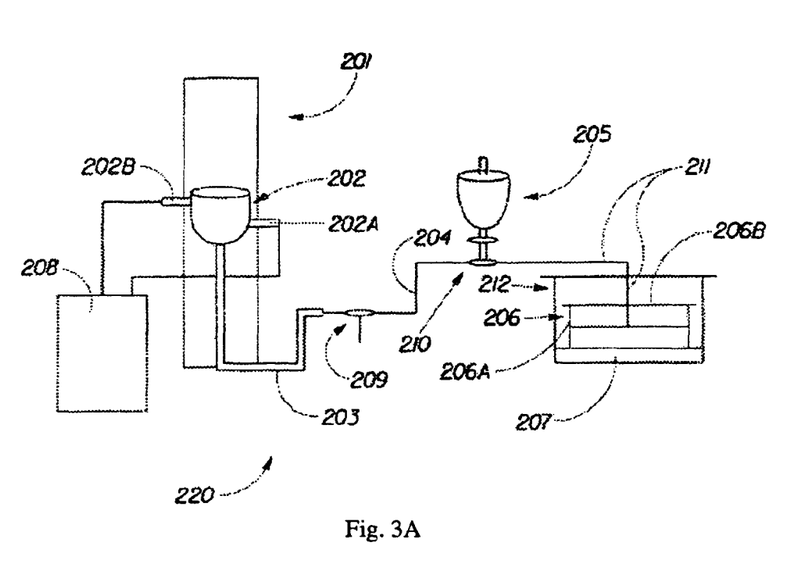
FIGS. 3A to 3C illustrate the Capillary Sorption Test

The capillary sorption equipment, depicted generally as 220 in FIG. 3A, is set up and operated under TAPPI conditions (50% RH, 23° C.). The sample is placed in a movable, temperature controlled, sample assembly 202 that is connected hydraulically to a fluid reservoir 206 that rests on a balance 207. The balance 207 should read to ±0.001 g and be capable of being interfaced to a computer system (not shown)

for control and collection of data. A suitable balance is available from Mettler Toledo as PR1203 (Hightstown, N.J.). The specific fluid path of the system is as follows: The bottom of the sample assembly 202 is connected to a 3-way glass stopcock 209 via Tygon® tubing 203. The stopcock 209 is connected either to drain or via glass tubing 204 to a second 3-way glass stopcock 210. This stopcock 210 switches between a filling reservoir 205 or the balance reservoir 206.

The balance reservoir 206 consists of a lightweight 12 cm diameter glass dish 206A with a plastic cover 206B. The cover 206B has a hole in its center through which the glass tubing 211 contacts the fluid in the balance reservoir 206. The glass tubing 211 must not touch the cover 206B or the balance reading will be invalid. The balance 207 and balance reservoir 206 are further enclosed in a Plexiglas® box 212 to minimize evaporation of the test fluid from the reservoir 206 and enhance balance stability during the procedure. The box 212 has a top and walls, where the top has a hole through which the tubing 211 is inserted. Once again the tubing 211 must not touch the box 212 or the balance reading will be invalid.

Detailed Description of Sample Assembly

Figure 3B:
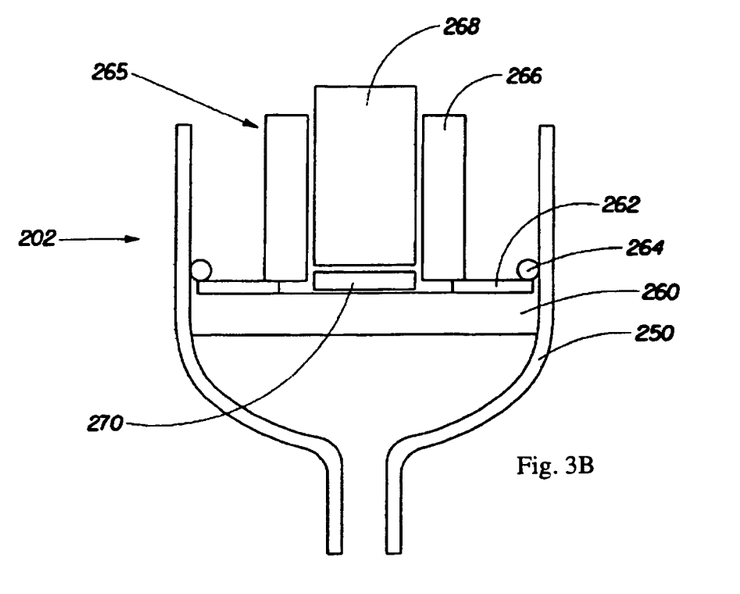

The sample assembly, generally depicted as 202, consists of a Buchner type funnel fitted with a glass fritted disc, a heated water jacket, and a piston/cylinder apparatus shown in more detail in FIG. 3B. The fritted disc funnel 205 has a capacity of approximately 350 mL with a porous glass frit 260 specified as having 4 to 5.5 μm pores (available from Corning Glass Co., Corning N.Y., part #36060-350F). The pores are fine enough to keep the frit surface wetted at the capillary suction heights specified (i.e., the fritted disc does not allow air to enter the continuous column of test liquid below the frit). The outside of the fritted disc funnel 205 is externally jacketed and connected to a heating bath 208 via inlet 202A and outlet 202B ports to maintain the assembly at a constant temperature of 31° C.

Figure 3C:
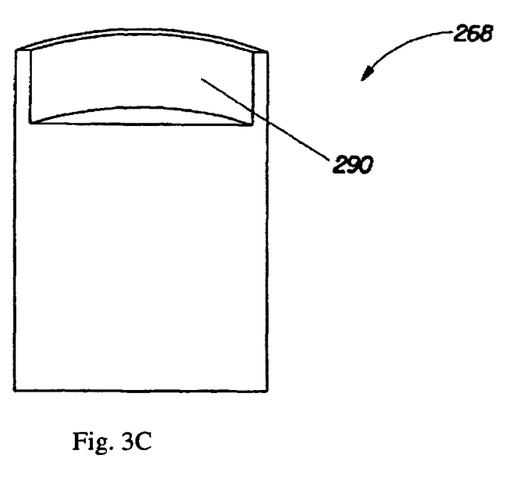

FIG. 3B is a cross-sectional view of 202 (shown without the water jacket) comprising the funnel 250, the glass frit 260, and the cylinder/piston assembly, shown generally as 265, that provides a small confining pressure to the test sample 270. The cylinder 266 is fabricated from Lexan® and has an outer diameter of 7.0 cm, an inner diameter of 6.0 cm and a height of 6.0 cm. The piston 268 is fabricated of Teflon® and has a diameter of 0.02 cm less than the inner diameter of cylinder 266, and a height of 6.0 cm. As shown in FIG. 3C, the top of the piston is center-bored to provide a chamber 290 that is 5.0 cm in diameter and 1.8 cm deep. This chamber accommodates optional weights used to adjust the total weight of the piston to provide a confining pressure of 1.4 kPa on the sample 270, based on the actual measured diameter of the dry sample.

To prevent excessive evaporation of test fluid from the glass frit 260, a Teflon® ring 262 is placed on the surface of the frit. The Teflon® ring is fabricated from sheet stock 0.127 mm thick (available from McMaster-Carr, Atlanta, Ga., as 8569K16) with an outer diameter of 7.6 cm and inner diameter of 6.3 cm. In addition, a Vitron® O-ring 264 (available from McMaster-Carr, Atlanta, Ga., as AS568A-150) is placed on top of the Teflon® ring 262, to further assist in prevention of evaporation. If necessary the O-ring should be sized to fit snugly around the inner wall of the glass funnel 250. To minimize air destabilization around the sample, a non-surfactant treated/incorporated, apertured film approximately 14 cm by 14 cm (not shown), is used to cover the sample assembly 202 during the experiment. The apertures are large enough to prevent condensation from forming on the underside of the film during the experiment.

The sample assembly 202 is mounted on a vertical slide, generally depicted as 201 in FIG. 3A, which is used to adjust the vertical height of the sample. The vertical slide may be a rodless actuator under computer control (computer not shown). A preferred actuator and motor drive are available from Industrial Devices (Novato, Calif.) as item 202X4X34N-1D4B-84-P-C-S-E, and from CompuMotor (Rohnert, Calif.) as ZETA 6104-83-135 respectively.

Equilibrium Endpoint Determination

Data from the balance is collected via computer throughout the capillary sorption experiment. While at each capillary suction height, balance readings are taken every 5 seconds. The delta flow, here defined as the change in balance reading divided by 5 seconds, is calculated for each time interval. When 50 consecutive intervals have a delta flow of less than 0.0005 g/sec the system is considered to have reached equilibrium.

Test Sample Preparation

The test sample can be obtained by punching out a 5.4 cm diameter circular-shaped structure from a storage absorbent member, using an arch punch. When the member is a component of an absorbent article, other components of the article must be removed prior to testing. In those situations where the member cannot be isolated from other components of the article without significantly altering its structure (e.g., density, relative disposition of the component materials, physical properties of constituent materials, etc.) or where the member is not a component of an absorbent article, the test sample is prepared by combining all the materials that constitute the member such that the combination is representative of the member in question. The dry weight of the test sample is recorded to ±0.001 g. The diameter of the sample is measured to ±0.01 mm using a suitable, calibrated Vernier caliper.

Experimental Set-Up

1. Using a clean, dry glass frit 260, attach the sample assembly 202 to the vertical slide 201. Move the assembly on the vertical slide such that the glass frit 260 is approximately at the 0 cm height. (0 cm is defined as the level the top of the glass frit 260 is aligned with the level of fluid in the balance reservoir 206.)
2. Set up the apparatus components as shown in FIG. 3A, as discussed above.
3. Place the balance reservoir 206 on the balance 207. Place the Plexiglas® box 212 over the balance and fluid reservoir aligning the holes such that the glass tube 211 can be inserted down through the box 212 and balance reservoir lid 206B without touching either.
4. Fill the filling reservoir 205 with test fluid. Turn stopcock 210 to connect the filling reservoir 205 and glass tubing 211, and fill balance reservoir 206.
5. Attach the Tygon® tubing 203 between stopcock 209 and the sample assembly 202. Level the glass frit 206 and turn stopcock 209 to connect the Tygon® tubing 203 and the glass tubing 204.
6. Turn stopcock 210 to connect the filling reservoir 205 and glass tubing 204 and allow test fluid to fill the sample funnel until the fluid level exceeds the top of the glass frit 260. Invert the sample funnel 250 and empty the fluid from on top of the glass frit. If necessary, remove all air bubbles from inside the Tygon® tubing 203 and any bubbles trapped below the glass frit 260, by allowing the air bubbles to rise and escape through the drain of stopcock 209.
7. Relevel the glass frit 260 using a small level that can fit inside the sample funnel 250 and on the actual surface of the glass frit. Zero the glass frit 260 such that the fluid reservoir 206 level is 10 mm below the top of the glass frit 260. To accomplish this, either adjust the amount of liquid in the balance reservoir 206, or reset the zero position on the vertical slide 201.

8. Attach the inlet 202A and outlet 202B ports of the sample assembly to the heating bath 208. Allow the temperature of the glass frit 260 to come to 31° C. and equilibrate for 30 minutes.

Capillary Sorption Procedure

1. After completing the experimental setup as described above, confirm that the heating bath is circulating through the sample assembly jacket and the glass frit disc 260 temperature is at 31° C.
2. Position the sample assembly 202 such that glass frit 260 at 200 cm suction height. Turn stopcocks 209 and 210 to connect the glass frit 260 with the balance reservoir 206. (The filling reservoir 205 is isolated by stopcock 210, and the drain is isolated by stopcock 209.) Equilibrate sample assembly 202 for 30 minutes. The cylinder 266, piston 268 and any necessary weights should also be equilibrated at 31° C. for 30 minutes at this time.
3. Close stopcocks 209 and 210, and move the sample assembly 202 to a point where the glass frit 260 is at 100 cm capillary suction height.
4. Place the Teflon ring 262 on the surface of the glass frit disc 260 followed by the Vitron® O-ring 264. Place the pre-heated cylinder 266 concentrically on the Teflon ring. Place the test sample 270 concentrically in the cylinder 266 on the surface of the glass frit 260. Insert the pre-heated piston 268 into the cylinder 266, along with any necessary confining weights. Cover the sample assembly 202 with the apertured film.
5. The balance reading at this point establishes the zero or tare reading.
6. Move the sample assembly 202 so that the glass frit 260 is at 200 cm capillary suction height. Turn stopcocks 209 and 210 to connect the glass frit 260 with the balance reservoir 206 and begin balance and time readings.
7. After reaching equilibrium (determined as described above), the height of the sample assembly 202 is adjusted to the next capillary suction height in the absorption/desorption cycle. The capillary suction heights for the complete cycle is as follows (all heights in cm): 200, 180, 160, 140, 120, 100, 90, 80, 70, 60, 50, 45, 40, 35, 30, 25, 20, 15, 10, 5, 0, 5, 10, 15, 20, 25, 30, 35, 40, 45, 50, 60, 70, 80, 90, 100, 120, 140, 160, 180, 200.

Glass Frit Correction (Blank Correct Uptake)

Since the glass frit disc 260 is a porous structure, the capillary sorption absorption uptake (blank correct uptake) must be determined and subtracted to get the absolute sample capillary sorption absorption uptake. The glass frit correction should be performed for each new glass frit used. Run the capillary sorption procedure as described above, except without test sample, to obtain the Blank Uptake (g). The elapsed time at each specified capillary suction height equals the Blank Time (s).

Evaporation Loss Correction

Even after taking all appropriate precautions listed above, some evaporative loss will occur. The sample evaporation is measured for each newly installed glass frit 260.

1. Move the sample assembly 202 such that the glass frit 260 is 2 cm above zero. Turn stopcocks 209 and 210 to connect the glass frit 260 with the balance reservoir 206. Allow system to equilibrate for 30 minutes.
2. Close stopcocks 209 and 210.
3. Place Teflon® ring 262 on surface of glass frit 260. Place Vitron® O-ring 264 on the Teflon® ring. Place the preheated cylinder 266 concentrically on the Teflon® ring. Insert the preheated piston 268 into the cylinder 266. Finally place the apertured film over sample assembly 202.

4. Turn stopcocks 209 and 210 to connect the glass frit 260 with the balance reservoir 206. Record balance reading and time for 3.5 hours.

Calculations

Sample Evaporation $$\text{Sample Evaporation (g/hr)} = \frac{(\text{balance reading at 1 hr}) - (\text{balance reading at 3.5 hr})}{2.5 \text{ hr}}$$

Blank Correct Uptake:

$$\text{Blank Correct Uptake (g)} = \text{Blank Uptake (g)} - \frac{\text{Blank Time(s)} * \text{Sample Evaporation(g/hr)}}{3600 \text{ (s/hr)}}$$

Capillary Suction Absorbent Capacity (CSAC):

$$CSAC \text{ (g/g)} = \frac{\text{Sample Uptake (g)} - \frac{\text{Sample Time (s)} * \text{Sample Evaporation (g/hr)}}{3600 \text{ (s/hr)}} - \text{Blank Correct Uptake (g)}}{\text{Dry Weight of Sample (g)}}$$

The Capillary Sorption Desorption Height at which the material has released x % of its capacity achieved at 0 cm (i.e. of CSAC 0), (CSDH x) expressed in cm; The Capillary Sorption Desorption Height at which the material has released 50% of its capacity (CSDH 50) is also referred to as Medium Desorption Pressure (MDP), expressed in cm (of water column).

The amount of the test liquid, which was absorbed from the material to reach 100% of its capacity, per g of the material is referred to as Maximum Uptake, expressed in (g/g) (g of test liquid per g of the material). Maximal uptake describes the material capacity (g/g) at the 0 cm height.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A diaper comprising:
   a liquid pervious topsheet;
   a liquid impervious backsheet;
   an acquisition system disposed between said liquid pervious topsheet and said liquid impervious backsheet; and a storage layer disposed between said acquisition system and said liquid impervious backsheet, wherein said storage layer comprises an absorbent gelling material, wherein the acquisition system comprises an upper acquisition layer and a lower acquisition layer, wherein said lower acquisition layer is disposed between said upper acquisition layer and said storage layer and wherein the lower acquisition layer comprises a liquid acquisition material, said liquid acquisition material comprising: first fibers and second fibers, wherein said first fibers are chemically cross-linked cellulose fibers and said second fibers being selected from the group consisting of: polyethylene, polypropylene, polyester, rayon, lyocell, and mixtures thereof, wherein said liquid acquisition material has a total dry weight, said first fibers have a first dry weight of from about 30 to about 90 percent of said total dry weight, and said second fibers have a second dry weight of from about 10 to about 20 percent of said total dry weight, and wherein said liquid acquisition material has a Medium Desorption Pressure value corresponding to a height between about 5 cm and about 20.5 cm.

2. A diaper according to claim 1, wherein the first dry weight is from about 80 to about 90 percent of the total dry weight.

3. A diaper according to claim 1, wherein the first fibers are chemically cross-linked by citric acid.

4. A diaper according to claim 1, wherein the second fibers are polyester fibers.

5. A diaper according to claim 1, wherein the liquid acquisition material is an air-laid material.

6. A diaper according to claim 1, wherein the liquid acquisition material has a maximum uptake of not less than about 10 g/g.

7. A diaper according to claim 1, wherein said liquid acquisition material comprises a binder.

8. A diaper according to claim 7, wherein said binder comprises a styrene-butadiene latex binder.

9. A diaper according to claim 1 wherein said diaper comprises a rear waist region, a front waist region and a crotch region between said rear and front waist regions, said diaper further comprising a fastening system, said fastening system comprising fastening members joined to the rear waist region and a landing zone joined to the front waist region and wherein said diaper forms legs and waist openings when said fastening members are joined to said landing zone.

* * * * *